United States Patent
Maurer et al.

(10) Patent No.: US 10,463,306 B2
(45) Date of Patent: Nov. 5, 2019

(54) MEDICAL MEASURING SYSTEM AND METHOD FOR PRODUCTION OF THE MEASURING SYSTEM

(71) Applicant: Novalung GmbH, Heilbronn (DE)

(72) Inventors: Andreas Maurer, Tübingen (DE); Sven Filipon, Heilbronn (DE); Matthias Beurer, Stuttgart (DE)

(73) Assignee: Novalung GmbH, Heilbronn (DE)

( * ) Notice: Subject to any disclaimer, the term of this patent is extended or adjusted under 35 U.S.C. 154(b) by 374 days.

(21) Appl. No.: 15/301,205

(22) PCT Filed: May 15, 2015

(86) PCT No.: PCT/EP2015/001000
§ 371 (c)(1),
(2) Date: Sep. 30, 2016

(87) PCT Pub. No.: WO2015/172890
PCT Pub. Date: Nov. 19, 2015

(65) Prior Publication Data
US 2017/0014077 A1    Jan. 19, 2017

(30) Foreign Application Priority Data

May 15, 2014   (EP) ..................................... 14001734

(51) Int. Cl.
*A61M 1/36* (2006.01)
*G01L 19/00* (2006.01)
*A61B 5/00* (2006.01)

(52) U.S. Cl.
CPC ......... *A61B 5/6866* (2013.01); *A61M 1/3639* (2013.01); *G01L 19/0023* (2013.01); *A61M 2207/00* (2013.01)

(58) Field of Classification Search
CPC .. G01L 9/0023; A61B 5/6866; A61M 1/3639; A61M 2205/3327; A61M 2207/00
See application file for complete search history.

(56) References Cited

U.S. PATENT DOCUMENTS 3,418,853 A    12/1968 Curtis
4,194,974 A *  3/1980 Jonsson ................. H01H 35/26
                                                210/90

(Continued)

FOREIGN PATENT DOCUMENTS

CN    1913825 A    2/2007
DE    29810331 U1  9/1998

(Continued)

OTHER PUBLICATIONS

Benchoff, B., "Injection Molding With Hot Glue", Hackaday, May 12, 2014, one page.*

*Primary Examiner* — Daniel S Larkin
(74) *Attorney, Agent, or Firm* — Dinsmore & Shohl LLP

(57) ABSTRACT

The invention relates to a medical technology measuring system (1) comprising a measuring device (10) for measuring a characteristic of a fluid—in particular, for pressure measurement—wherein the measuring device comprises a lead (20) which extends along a central longitudinal axis (M) and is equipped to guide a fluid—in particular, blood—inside a longitudinal cavity (24) enclosed by a wall, and a sensor device (30) comprising a sensor (32) which is equipped to measure a characteristic of the fluid guided in the longitudinal cavity, wherein the measuring system (1) has an overmolding (9) which at least partially surrounds the measuring device (10)—preferably, both at least the sensor device (30) and also a section of the lead (20). As a result, the measuring device can be fastened and positioned on the lead in a simple and/or reliable, robust manner. The inven- (Continued)

tion further relates to a method for producing such a medical technology measuring system.

22 Claims, 8 Drawing Sheets

(56) References Cited

U.S. PATENT DOCUMENTS

| | | | |
|---|---|---|---|
| 4,263,808 A | 4/1981 | Bellotti et al. | |
| 4,425,918 A | 1/1984 | Moll et al. | |
| 4,431,009 A | 2/1984 | Marino, Jr. et al. | |
| 4,443,407 A | 4/1984 | Weinberg et al. | |
| 4,734,184 A | 3/1988 | Burleigh et al. | |
| 4,924,872 A | 5/1990 | Frank | |
| 5,105,820 A | 4/1992 | Moriuchi et al. | |
| 5,148,811 A | 9/1992 | Messinger | |
| 5,237,999 A | 8/1993 | von Berg | |
| 5,351,686 A | 10/1994 | Steuer et al. | |
| 5,370,123 A | 12/1994 | Shinzato | |
| 5,387,329 A | 2/1995 | Foos et al. | |
| 5,581,038 A | 12/1996 | Lampropoulos et al. | |
| 5,614,677 A | 3/1997 | Wamsiedler et al. | |
| 5,925,830 A | 7/1999 | Schalk | |
| 5,965,089 A | 10/1999 | Jarvik et al. | |
| 6,136,136 A * | 10/2000 | Heider | C08G 18/12 156/331.4 |
| 6,272,930 B1 | 8/2001 | Crozafon et al. | |
| 6,725,726 B1 | 4/2004 | Adolfs et al. | |
| 6,880,404 B2 | 4/2005 | Uberreiter | |
| 6,887,214 B1 | 5/2005 | Levin et al. | |
| 7,025,750 B2 | 4/2006 | Brugger et al. | |
| 7,059,195 B1 | 6/2006 | Liu et al. | |
| 7,108,672 B2 | 9/2006 | Steele et al. | |
| 7,313,968 B2 | 1/2008 | Kaneko et al. | |
| 7,410,473 B2 | 8/2008 | Levin et al. | |
| 7,748,275 B2 | 7/2010 | Kouda et al. | |
| 7,771,380 B2 | 8/2010 | Jonsson et al. | |
| 7,856,887 B2 | 12/2010 | Klees et al. | |
| 7,879,241 B2 | 2/2011 | Sparks et al. | |
| 7,921,723 B2 | 4/2011 | Reiter et al. | |
| 8,506,684 B2 | 8/2013 | Weaver et al. | |
| 8,721,883 B2 | 5/2014 | Lauer | |
| 9,186,072 B2 | 11/2015 | Manstrom et al. | |
| 9,551,625 B2 | 1/2017 | Brugger et al. | |
| 9,808,567 B2 | 11/2017 | O'Mahony | |
| 9,883,888 B2 | 2/2018 | Frey et al. | |
| 2002/0073782 A1 | 6/2002 | Chevallet et al. | |
| 2004/0039290 A1 | 2/2004 | Narimatsu et al. | |
| 2005/0284815 A1 | 12/2005 | Sparks et al. | |
| 2007/0261496 A1 | 11/2007 | Jonsson et al. | |
| 2010/0114063 A1 | 5/2010 | Recinella et al. | |
| 2012/0258545 A1 | 10/2012 | Ash et al. | |
| 2014/0076058 A1 * | 3/2014 | Brugger | G01L 9/0041 73/723 |

FOREIGN PATENT DOCUMENTS

| | | |
|---|---|---|
| DE | 102013012433 A1 | 1/2015 |
| EP | 0330891 A1 | 9/1989 |
| EP | 0688531 A1 | 12/1995 |
| EP | 0762084 A2 | 3/1997 |
| EP | 0993266 A1 | 4/2000 |
| JP | H03258235 | 11/1991 |
| JP | 2005311321 A | 11/2005 |
| JP | 2008296061 A | 12/2008 |
| JP | 2009200172 A | 9/2009 |
| JP | 2011222782 A | 11/2011 |
| JP | 201432190 A | 2/2014 |
| WO | WO-1997015228 A1 | 5/1997 |
| WO | WO-2012127422 A1 | 9/2012 |

* cited by examiner

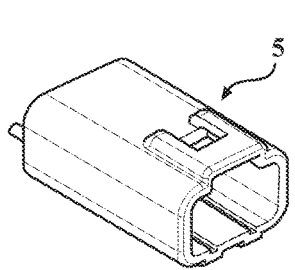
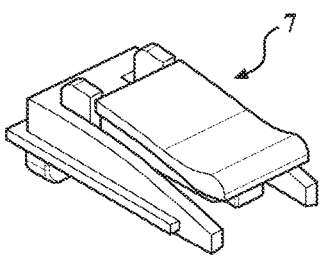
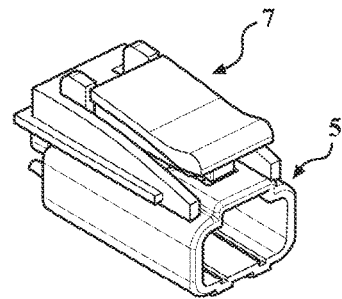
FIG. 3A  FIG. 3B  FIG. 3C
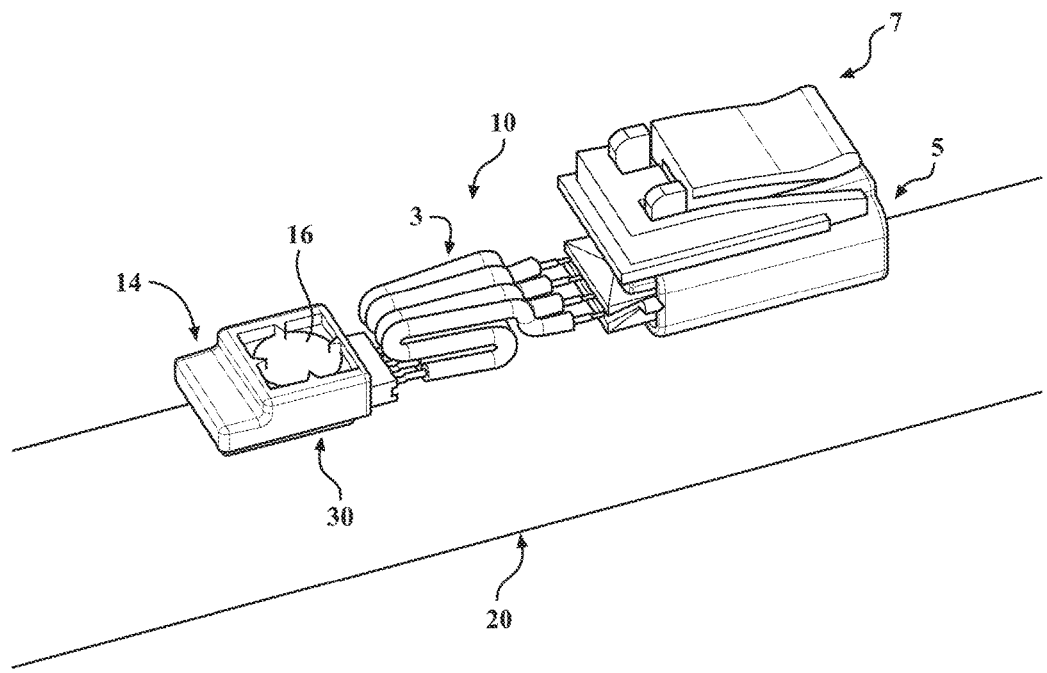
FIG. 4A

MEDICAL MEASURING SYSTEM AND METHOD FOR PRODUCTION OF THE MEASURING SYSTEM

CROSS-REFERNCE TO RELATED APPLICATIONS

This application is a U.S. national phase of international application No. PCT/EP 2015/001000, filed May 15, 2015, which claims priority to European application No. EP 14001734.4,filed May 15, 2014,each of which are incorporated herein in their entirely.

FIELD OF THE INVENTION

The present invention relates to a medical technology measuring system comprising a measuring device for measuring a characteristic of a fluid—in particular, for pressure measurement—wherein the measuring device comprises a lead which extends along a central longitudinal axis and is equipped to guide a fluid—in particular, blood—inside a longitudinal cavity enclosed by a wall, and a sensor device comprising a sensor which is equipped to measure a characteristic of the fluid guided in the longitudinal cavity. The invention further relates to a method for producing such a medical technology measuring system. The present invention relates in particular to a medical technology measuring system with individual features of claim 1, as well as to a method with individual features of the independent method claim.

BACKGROUND OF THE INVENTION

Measuring devices or sensors are known which are arranged on a connector, adapter, or intermediate piece between individual sections of a lead. The lead conducts a fluid—in particular, an isotonic saline solution or other crystalloid infusion solutions or blood—whose characteristic, e.g., pressure, is supposed to be recorded. In the case of such measuring devices, there is frequently the risk of coagulation (or so-called blood clotting) or hemolysis—in particular, due to any edges, undercuts, or fluidically unfavorable transitions. The fasteners or connectors also increase the risk of leakage and have to be checked as well. In the process, leaks can occur—in particular, at the interfaces between a connector and an extracorporeal lead/hose set or in the measuring system. Also, the connector or adapter has to be mounted on the lead, and a seal, bond, or other interface that is as sterile as possible or sterilizable must be ensured.

As an alternative to measuring devices or sensors coupled or integrated in the lead, a measurement can also take place outside of the lead. The corresponding sensor can then record pressure indirectly, e.g., by means of a water column. However, in the case of this type of measurement, a so-called priming operation is required to be able to start the measurement. In the case of priming, the lead/hose set is filled with a crystalloid solution such as, for example, an isotonic saline solution (NaCl), and, thereupon, a complete ventilation takes place. There is a risk that the ventilation of the lead/hose system will be incorrectly performed. Due to blood penetrating sections of the lead leading to a measuring sensor during the measurement in the crystalloid solution, and its coagulation, the measuring operation is impaired or interrupted, which can be life-threatening.

Also disadvantageous in the case of this type of measurement are measuring errors, which are caused by gas pockets in the water column. Also, the measurement itself is usually delayed, since a pressure wave must first be transferred through the water. As a result, the indirect measurement makes synchronization of a pump with the arterial pressure curve of the patient, for example, difficult.

Apart from the question of which device the pressure should be measured by, the measuring device should be technically designed such that the measuring devices can be fastened to a lead in a robust or reliable and fluid-tight manner. A secure fastening is in particular necessary when the measuring device cannot or should not be arranged in connection with a connector, adapter, or intermediate piece of the lead.

SUMMARY OF THE INVENTION

One problem addressed by the present invention is that of providing a measuring system, in which a measuring device can be fastened fluid-tight and positioned in a simple and/or secure, robust manner on a lead. In the process, the invention also addresses the problem of providing a method by means of which the measuring device can be fixed on a lead, e.g., on a hose of an extracorporeal blood-carrying hose system—in particular, on a flexible lead—in order to form a measuring system. The measuring device can, in the process, comprise a plurality of components, including a sensor and one or more cables.

The invention is based upon a medical technology measuring system with a measuring device for measuring a characteristic of a fluid—in particular, for pressure measurement—wherein the measuring device comprises:
  a lead—in particular, a hose lead—which extends along a central longitudinal axis and is equipped to guide a fluid—in particular, blood—inside a longitudinal cavity enclosed by a wall;
  a sensor device with a sensor, comprising a sensor which is equipped to measure a characteristic of the fluid guided in the longitudinal cavity.

In accordance with the invention, provision is made for the measuring system to have an overmolding, which at least partially surrounds the measuring device. In one advantageous updated version of the invention, the overmolding surrounds at least the sensor device, as well as a section of the lead.

As a result of this inventive measure, the sensor device can be fastened and positioned directly on the lead in a fluid-tight manner. Additional components such as, for example, an adapter, an intermediate piece, or a connector for mounting the sensor device on the lead can be advantageously dispensed with.

In the process, the molding can form a housing for the measuring system, or at least for individual parts of the measuring system. Preferably, the overmolding has, at least in sections, a circumferential closed contour—in particular, a circumferential lateral surface—as a result of which the overmolding can be connected to the lead in a stable or robust manner. According to one variant, the overmolding has convexly curved surface sections—in particular, convexly curved surface sections on several levels—especially on a level orthogonal to the central longitudinal axis and also on a level parallel to the central longitudinal axis. This enables a three-dimensional outer contour, which can be integrated in an expedient manner to an outer lateral surface of a lead. The radial dimensions can in the process be minimized in the respective section of the overmolding, and the overmolding can also be optimized with regard to ergonomics. In the process, all surface sections can be curved convexly (outward).

The overmolding can, for example, be provided by a bonding method or an overmold method or a casting method. In the process, the molding can ensure a mechanical protection of the sensor device. Preferably, the overmolding is designed to be blood and/or water repellent.

By measuring device is preferably meant a device that can guide or conduct a specified fluid in a specified condition—in particular, in a flow condition—toward or away, and can record a characteristic, e.g., the pressure, of the fluid and, optionally, can also at least evaluate said characteristic to some extent. Such a measuring device can, for example, be used for an invasive pressure measurement, or in conjunction with an extracorporeal circulation, e.g., for kidney replacement, for cardio-pulmonary support or liver support, or for measurement of the infusion pressure or injection pressure in fluid-conducting medical products. Particularly in the case of an invasive/implanted arrangement, the advantages of a good seal and/or sterility can also thereby obtain. Along with a sensor, the measuring device can have additional components such as, for example, a protective cap, a receptacle, or a preferably water-repellent membrane, wherein the membrane can ensure protection of the sensor from external influences. By means of the measuring device, vital functions, for example, of a patient can be monitored, e.g., heart muscle contractions (hemodynamics), or a pressure loss caused by extracorporeal circulation can be measured.

By fluid is preferably meant a liquid; however, the fluid can also be a gas, or at least have gaseous components. A characteristic of the fluid may, thereby, be understood to be a physical or chemical quantity of the fluid or a quantity describing the state of the fluid, for example. A characteristic can, for example, be described by a specific proportion of a gaseous component, e.g., a $CO_2$ or $O_2$ content by volume.

In the process, by lead is preferably meant every type of lead which can be used in conjunction with medical care, diagnosis, or therapy, e.g., also in conjunction with any catheters. The lead can in the process also be part of a set of medical instruments. The—in particular, blood-carrying—lead can be part of a so-called lead/hose set, or can constitute this lead/hose set. The lead can in the process also comprise a cannula which ensures access to the body or be configured as a cannula in sections. The lead can also be formed by another fluid-carrying, hollow body. Preferably, the lead is flexible at least in sections, and thus elastically formable. In particular, the lead can be curved or arched. In the process, the elasticity of the lead is not influenced, or not influenced perceptibly, by the sensor device. The diameter of the lead can, to a large extent, be freely selected. In particular, inside diameters of, for example, 3/8" (9.52 mm) or 1/4" (6.35 mm) are expedient.

The wall or also the entire lead can be made of a flexible plastic material—in particular, of polyvinyl chloride (PVC) material. Preferably, the plastic material is an ultra-pure, phthalate-free, soft PVC. In the simplest case, the lead is, for example, a PVC hose frequently used in medical technology. The thickness of the wall and/or lead is in the range of 1 mm to 5 mm—preferably in the range of 1.2 mm to 3.5 mm, further preferably in the range of 1.5 mm to 3 mm, and, in particular, in the range of 1.6 mm to 2.4 mm.

In the process, by sensor device is preferably meant a component of the measuring device, by means of which a measuring signal, e.g., a pressure signal, can be recorded, and either processed or at least forwarded.

In the process, by sensor is preferably meant a component of the measuring device, by means of which a measuring signal, e.g., a pressure signal, can be at least recorded. For example, a piezo-resistive sensor can be used. Optionally, sensors can also be used that are based upon one or more of the following physical principles or functionalities: e.g., piezoelectric, capacitive, inductive, frequency analog, or sensors with Hall element, fiber optic sensors. In the process, the sensor can be adapted to its surface facing the fluid/blood in the contour of the inner lumen of the lead, such that a continuous and seamless transition between the sensor and the inner lumen is ensured—in particular, in order to prevent coagulation and hemolysis in the region of the sensor.

In the process, by overmolding is preferably meant a jacket made of filling material or a housing, which provides, at least partially, an outer surface of the measuring system. The filling material is preferably a material which is moldable by means of the injection molding method—in particular, by means of so-called "hotmelt molding" or "macromelt molding" or low-pressure molding technology.

According to one exemplary embodiment, the overmolding is provided on the lead such that the overmolding surrounds at least the sensor device or also additional components of the measuring device, wherein at least the sensor device is positioned—in particular, embedded—in a predefined position relative to the lead in the overmolding. As a result, the sensor device can be supported at least partially by the overmolding also—in particular, radially outward—and the interface between wall and sensor device can be designed to be relatively robust. The sensor device can also be fixed directly on the wall, of course. However, the overmolding can prevent external forces from affecting the sensor device, and a predetermined set position of the sensor device, optionally, also without any specified type of connection—in particular, without the requirement of a cohesive connection—from being ensured.

According to one exemplary embodiment, the overmolding is made of a hotmelt adhesive. The use of a hotmelt adhesive furnishes the advantages, whether in the handling or in the production of the measuring system, described in detail in what follows.

According to one exemplary embodiment, the overmolding is made of a mixture of polyester and hydrocarbon resin. As a result of this, good adhesion on the lead can be ensured and, further, good resistance—and also good haptic properties. Preferably, the overmolding has a higher percentage of polyester than of hydrocarbon resin—in particular, at least 60 parts per 100. Also, preferably, the overmolding is formed by a mixture of at least 70 parts polyester. According to one preferable variant, the overmolding is formed by a mixture of 75 to 85 parts polyester and 15 to 25 parts hydrocarbon resin. This mixture also provides, in particular, a good compromise between flow behavior and drying behavior. It turns out that a mixing ratio of at least approximately 80 parts polyester and at least approximately 20 parts hydrocarbon resin can ensure especially advantageous material characteristics. A ratio of 80 to 20 can in the process be preferable for many applications. According to one variant, the mixture can also have color pigments—in particular, in the range of 1 to 3 parts, and preferably, 1.5 parts. If color pigments are provided, the portion of polyester and/or hydrocarbon resin can be correspondingly reduced. In the process, these are preferably weight portions.

It turns out that, in the event of a mixture of polyester and hydrocarbon resin, by means of the polyester, a good isopropyl resistance can be ensured. In addition, polyester can ensure a good elasticity of the overmolding in the final product. Polyester has a comparatively high viscosity in the operational process.

It also turns out that, in the event of a mixture of polyester and hydrocarbon resin, by means of the hydrocarbon resin, a good surface adhesion can be ensured—in particular, on PVC tubes. Furthermore, hydrocarbon resin can ensure the rigidity or deformation resistance of the overmolding. Hydrocarbon resin has a comparatively high viscosity in the operational process.

The density of the overmolding is preferably 0.9 to 0.95 kg/m3. The surface of the overmolding is preferably smooth and has no pores. The surface is preferably closed-porous.

With a hotmelt adhesive material, a good adhesion to PVC tubes can, in particular, also be ensured. It turns out that, in comparison to polyamide-based hotmelts, this overmolding material has especially good adhesion to PVC tubes and also an especially good isopropyl resistance. The isopropyl resistance is advantageous in that the overmolding can be disinfected with conventional disinfectants, without the surface changing. The surface of the overmolding remains resistant upon contact with disinfectants. It does not get sticky and also does not decompose. These advantages were also observed in comparison to materials based upon synthetic rubber or synthetic polymers. It turns out, in addition, that this overmolding material has a good elasticity—in particular, in the case of thicknesses of up to about 1.4 mm.

The overmolding material can, for example, be provided in granulate form. The overmolding material can, for example, be black in color or coloration. The viscosity of the overmolding material can, for example, be in the range of 20,000±5,000 mPa·s, measured in accordance with DIN 53019 (at 190° C.). The melting point of the overmolding material can, for example, be 165° C.+/−3°, measured in a Kofler bench, and thus in a Kofler heating stage. The open time can be about 40 sec. The overmolding material can have a shrinkage behavior of, for example, circa −2%.

In the process, the molding can also fulfill a damping function. In other words, the measuring system can also be implemented to be especially robust, due to the overmolding. In the process, the overmolding can also be made of a material with a high elasticity—in particular, with at least 70 parts polyester per 100, and preferably 80 parts per 100. The elasticity of the overmolding also has the advantage that the lead remains flexible, and that the overmolding does not readily detach from the lead, even in the case of increased relative movements or longer periods of application of the measuring system.

According to one exemplary embodiment, the overmolding is configured to adhere to the outer lateral surface of the wall—in particular, by physical binding to the wall. As a result, the overmolding can be positioned in a precise position relative to the lead and, as a result, also position other components of the measuring device. In the process, a chemical bond of the overmolding material to the wall is not necessary. Instead, the adhesion can be ensured simply by the physical bond—in particular, by mechanical adhesion. It turns out that the physical adhesion can be well ensured with an overmolding material made of polyester and hydrocarbon resin—in particular, on PVC tubes.

According to one exemplary embodiment, the overmolding completely surrounds at least the lead, at least in sections—in particular, on at least two sections of the overmolding spaced apart from one another—preferably, on two free ends of the overmolding arranged at a maximum distance from one another. As a result, the overmolding can be connected to the lead in a secure and robust manner—in particular, in the region of a proximal and/or distal end or section of the overmolding. In the process, the overmolding can have one or more recesses on an underside of the measuring system. In the process, a recess can, for one thing, enable an improved flexibility of the system, even in the case of an overmolding material with a comparatively low elasticity. For another thing, a recess can also ensure that the sensor can be seen from the other side of the lead (i.e., from the underside of the overmolding). The recess can therefore also fulfill the function of a window.

According to one exemplary embodiment, further components of the measuring system—in particular, a receptacle or, optionally, also an adapter cable—are positioned relative to the lead by means of the overmolding and supported in a predetermined position relative to one another and/or relative to the lead in the overmolding, wherein the overmolding surrounds or embeds these components at least partially (in particular, radially outward). As a result, it is not necessary to fix the receptacle in some way on the lead. The receptacle can be held in position by means of the overmolding. The adapter cable and/or the receptacle can be surrounded at least partially by the overmolding.

In the process, the molding can surround both the lead as well as also further components of the measuring system, except for an optionally provided button for actuation of the sensor device, and form an integral housing in which the further components are integrated.

According to one exemplary embodiment, the lead is directly connected—in particular, firmly bonded—to the sensor device—in particular, by means of an adhesive agent. As a result, a precise position of the sensor can be defined via the position of the sensor device, regardless of any elastic characteristics of the overmolding. In the process, at least one further component of the measuring system, in which case an exact positioning is not necessary or desired, can be indirectly connected to the lead via the overmolding or can be positioned relative to the lead by means of the overmolding.

According to one exemplary embodiment, the overmolding has an extension or an edge on a proximal and/or distal end or section of the overmolding, which comes into contact with the outer lateral surface of the wall and is configured to align the lead and stabilize it within the overmolding. As a result, kink protection can be provided. The extension can prevent the lead from being subjected to especially heavy loads where the overmolding begins or even kinks. Preferably, the extension is configured to be completely circumferential. Additionally, the extension is preferably configured to be tubular. The extension preferably has a thickness of up to a maximum of 1.4 mm, which can ensure a good elasticity. The extension preferably has a length in the range of 5 mm to 20 mm, further preferably, of 7 mm to 15 mm, and especially preferably, of 8 mm to 10 mm. Such a length can ensure that a bend of the lead is conveyed in the overmolding such that the overmolding adheres well on the lead, even in the case of frequent or strong relative movements.

According to one exemplary embodiment, the overmolding has an opening extending preferably in a radial direction—in particular, at least approximately vertically/orthogonally to the central longitudinal axis—wherein the opening provides a connection (a communications path) between the sensor and the surroundings. The sensor is connected to the surroundings through the opening. As a result, the overmolding can essentially completely embed the measuring device and support and position it in several directions and levels, without interrupting a connection of the sensor of the sensor device to the surroundings or having to establish a connection via an additional lead or implementation. Preferably, the opening extends in a radial direction—in particular, at least approximately vertically/orthogonally to the central longitudinal axis.

According to one exemplary embodiment, the measuring system has a receptacle, wherein the overmolding surrounds the receptacle at least partially and is preferably also provided between the lead and the receptacle. In other words, the receptacle is also embedded on an underside in the overmolding and is positioned solely by means of the overmolding relative to the lead. The receptacle does not directly contact the lead, but, rather, is only indirectly connected to the lead via the overmolding. As a result, situations in which the receptacle rubs against the outer lateral surface of the lead in the event of handling—in particular, bending—of the lead can be prevented. A relative movement between a comparatively hard material of the receptacle and of the lead can be largely avoided. The overmolding can act as a damping element between the receptacle and the lead, which is expedient, in particular, in the case of receptacles with comparatively large extensions.

According to one exemplary embodiment, the overmolding overlaps the sensor device in a longitudinal direction along the central longitudinal axis in both directions, wherein the overmolding preferably has a front side, which, in a longitudinal direction, is arranged at least approximately flush in a plane with a front-side end of a component of the measuring system—in particular, flush with the sensor device and/or a/the receptacle of the measuring device. As a result, an arrangement can be provided, in which also further components of the overmolding are protected and are embedded in the overmolding, such that the further components do not jam with other objects or are not damaged on any parts protruding from the overmolding.

According to one exemplary embodiment, the measuring system has an adapter cable connected to the sensor device, which is embedded in the overmolding, wherein the adapter cable preferably is arranged with excess length—in particular, in a serpentine line—in the overmolding. As a result, the sensor device can be connected to a receptacle, without a relative movement between the receptacle and the sensor device causing tensile strains on the sensor device. In the case of such an arrangement, the lead can still have a high flexibility and can be handled as usual. The overmolding can be made of a comparatively soft material, and relative movements between the components of the measuring system can be compensated for due to the excess length. Additional holders for the cable are unnecessary. Bending the lead does not lead to tension within the measuring system. As a result, it can be ensured that, even in the event of careless handling of the lead, the sensor device remains positioned fluid-tight on the lead, with a high safety factor. The adapter cable also enables an embedding of the receptacle in the overmolding, without having to additionally fix the receptacle on the lead.

According to one exemplary embodiment, the overmolding is ergonomically formed for the inner surface of a human hand—in particular, with at least one convex outer surface section, which is curved convexly in a circumferential direction and in relation to the central longitudinal axis. As a result, the lead can be grasped and held, and handled in the region of the overmolding. Even thin leads with a diameter of, for example, ⅛ inch (3.17 mm) can, as a result, be handled in an ergonomic manner. In the process, the overmolding can also have a geometry adapted in relation to the handling of the system, or a geometry which indicates the flow direction of the blood or the position of the sensor opening and of the connector.

According to one exemplary embodiment, the overmolding tapers in at least one direction along the central longitudinal axis—in particular, from a plug-side rear to a front section, on which the sensor device is arranged. As a result, the quantity of necessary materials can be minimized, particularly in conjunction with an injection molding process. As a result, it is also possible to indicate to a user at a glance in which direction the lead surrounded by the overmolding is conducting the fluid, which further increases the practicability of the measuring system.

According to one exemplary embodiment, the lead has a radial cavity incorporated in the wall in radial direction, in which at least the sensor of the sensor device is arranged and is integrated in the wall such that the sensor is in communication with the fluid conducted in the longitudinal cavity. As a result, it can be ensured that the sensor device can be combined into a measuring unit in conjunction with the overmolding. The direct arrangement in the wall, i.e., the integration into the wall, also has the advantage that the flexibility of the lead is not decreased, and that a specific position can be selected for the measuring unit in a simple manner.

Further, through the arrangement of the sensor of the sensor device in the radial cavity of the wall, a mechanical protection of the sensor device, and thus of the measuring system on the lead, can also be achieved, which supplements the firmly bonded connection through the overmolding in advantageous manner.

In recent years, sensors have been available with ever smaller dimensions. This enables an advantageous arrangement of the sensor in close proximity to the fluid to be measured. The integrated sensor can be arranged directly on the fluid flow, without influencing the fluid flow. This also enables an especially precise measurement. In this connection, for example, an integration into a wall can also take place, which has a wall thickness in the range of only 1 mm to 3 mm.

Such an arrangement of the sensor also enables a largely random selection of the position of the sensor at any section or any circumferential position along the lead.

The arrangement of the sensor integrated into the wall makes intermediate pieces, couplings, or other connections unnecessary. For example, no Luer connections or other accesses to the lead are necessary. As a result, the risk of leakage or any unsterile interfaces can be significantly reduced. In addition, faulty operation of any connections can be prevented. For example, it is possible to prevent air from being drawn into the lead/hose system or into the catheter in the region of the measurement arrangement in an extracorporeal lead/hose system (such as, for example, in case of dialysis, cardio-pulmonary support or cardio-pulmonary bypass in cardiac surgery, or in a catheter or a sheath, e.g., in cardiology) in a section with negative pressure (in particular, lower pressure than atmospheric pressure), or to prevent fluid/blood from escaping from the bloodstream in a section with positive pressure (in particular, where blood is returned to the body).

In the process, a priming operation, —in particular, in relation to the sensor—is no longer necessary, which can save time and can make measurement in specific (e.g., life-threatening) situations especially useful. There are no longer any additional leads or hoses to be ventilated. In other words, the integrated arrangement of the sensor makes an "inline" measurement possible without time delay. The blood-carrying lead/hose system (including any catheter or cannula that is present) can in the process be filled and ventilated separately from a measurement.

In the process, a measurement can be executed at different positions. In particular, in the process, pressure can be measured at several measurement positions—in particular, as a function of a respective medical application—e.g., a suction pressure at a first position before a pump, a pump pressure at a second position after the pump, and a further pressure at a third position—in particular, a reperfusion pressure after a membrane ventilator. In other words, the measuring device can optionally also have a plurality of sensor devices, or at least a plurality of sensors. Accordingly, the lead or the catheter or the cannula can also have a plurality of radial cavities.

In the process, by radial cavity, a recess, a borehole, or also a hollowed out region or section or registration volume is meant. The radial cavity can also be formed by a longitudinal cavity extending in a radial direction which is only accessible from one side of the wall. The radial cavity does not necessarily have to be a grommet or a hole in the wall.

In the process, by opening is preferably meant an aperture or a radial cavity which completely penetrates the wall, and is thus provided continuously through the wall.

In the process, by recess is preferably meant a cavity extending in radial direction of an inside of the wall—hence, an inner lateral surface—which does not necessarily have to proceed to an outer lateral surface of the wall. In other words, the recess is not necessarily a hole in the wall, but, rather, can also hollow out the wall in a radial direction in sections.

In the process, by an arrangement "in communication with" is preferably meant an arrangement in which the sensor is in direct contact with the fluid. The sensor can be arranged in the fluid flow or on the side of the fluid flow or on the side of a flow path of the fluid flow.

In the process, the sensor device or the sensor can be part of the wall. The sensor can be arranged on an outside edge of the longitudinal cavity and delimit the longitudinal cavity in a radial direction. The sensor can extend at least approximately over the entire cross section profile of the radial cavity and have at least approximately the same expanse as a diameter or an expanse of the radial cavity. The sensor device can be configured to position the sensor in a radial position predefined by means of the radial cavity.

According to one exemplary embodiment, the radial cavity, together with the sensor device and/or the sensor, forms an interference fit, at which the wall can be sealed fluid-tight. As a result, this interface can be sealed to be largely separate from any firmly bonded connection. In the process, by interference fit is preferably meant an interface, in which one of the components to be coupled has a specified measurement, through which it can be ensured that the two components to be coupled can only be connected to one another in the event of a geometric adjustment to one another, and that, in any event, a play-free and gap-free connection is ensured. The radial cavity can, for example, be a borehole, which is preferably provided continuously through the wall—in particular, a cylindrical borehole with uniform diameter. The sensor or a free end of the sensor device protruding radially inward can be arranged flush to an inner lateral surface of the wall. As a result, favorable flow conditions can be ensured. Turbulence caused by undercuts or edges can be avoided to a large extent. As a result, the risk of blood clots or hemolysis can also be reduced. In the process, the sensor can be arranged in a radial position, which corresponds at least approximately to a radial distance of an inner lateral surface of the lead in the region of the radial cavity. The sensor device can have a contact section, which, at least in the region of the radial cavity—in particular, circumferentially around the radial cavity—is designed to geometrically correspond to an outer lateral surface of the lead or wall. As a result, the sensor device can be connected in a simple and robust manner to the lead—in particular, so as to adhere circumferentially around the region of the radial cavity to the lead.

In the process, by contact section is preferably meant a flat section, at which the sensor device can be attached on the lead. Preferably, the contact section is also dimensionally stable, and thus not elastically or plastically deformable, so that a relative movement between the lead and the contact section in the region of the radial cavity can be prevented. This can ensure a permanent, secure connection between these two components. The contact section can, for example, have a concave contour, which is designed to geometrically correspond to a convex contour of the lead or wall. As a result, for one thing, a relatively robust, resilient flat connection between the lead and the contact section can be ensured. For another thing, it is possible to effectively prevent the lead from turning, relative to the sensor device. In other words, this corresponding geometry can ensure the fluid-tightness at the interface between the sensor and the lead, even if no adhesive agent is provided at this interface, but, rather, only an interference fit, for example.

The contact section can, at least in the region of the radial cavity—in particular, circumferentially around the radial cavity—be firmly bonded to an/the outer lateral surface of the lead or wall—in particular, by means of an adhesive agent. As a result, the sensor device can be fixed on the lead in a robust manner. The firmly bonded connection in the region of the outer lateral surface also has the advantage that an adhesive agent—in particular, glue—does not necessarily have to be provided on an inner surface of the radial cavity. As a result, the fluid—in particular, blood—can be prevented from coming into contact with the adhesive agent. According to one variant, the sensor device can be connected to the wall solely by means of the overmolding material—in particular, in the case of a contact section specially equipped and geometrically designed for this.

The sensor device can be directly attached on an inner surface of the radial cavity without an adhesive agent, precisely and fluid-tight. The inner surface of the radial cavity can, for example, be cylindrical or have a polygonal cross section. The radial cavity is not necessarily round or circular, but, rather, can have any cross section. Preferably, the radial cavity is circular. This facilitates a precise arrangement of the sensor device or of the sensor in the radial cavity.

According to one exemplary embodiment, the measuring device and/or the measuring system is a disposable device provided for single use, wherein the sensor device preferably has a coupling point for communication and/or power supply—in particular, for a wired transmission via a cable or for a wireless transmission. The overmolding facilitates a simply built measuring device, in which, for instance, only a cable or a stick has to be removed, before the measuring device is disposed of. In the process, the measuring device can be optimized by at least one of the following measures with regard to suitability as a disposable device: lower ratio of materials, especially in the case of the overmolding, low number of components or production steps, and more efficient overmolding process (in particular, low energy requirements).

The above specified aim can also be achieved by a medical technology measuring system comprising a measuring device for measuring a characteristic of a fluid—in particular, for pressure measurement—in which the measuring system is formed by overmolding a lead, and a sensor device of the measuring device arranged on the lead—in particular, with a hotmelt adhesive. In this connection, the previously described advantages obtain.

The above specified aim can also be achieved by a method for producing a medical technology measuring system. The invention is based in particular upon a method for producing a medical technology measuring system—in particular, a measuring system according to one of the preceding claims, comprising the steps of providing a lead—in particular, a hose lead—that is equipped to guide a fluid—in particular, blood, and arranging a sensor device and, optionally, further components of the measuring system on the lead—in particular, on an outer lateral surface of a wall of the lead.

In accordance with the invention, in addition, the following procedural steps are provided: arrangement of the measuring system with the lead in an (overmolding) tool, and overmolding at least the sensor device and the lead, in each case at least in sections—in particular, with a material based upon polyester and hydrocarbon resin. As a result, the advantages described previously in conjunction with the measuring system, in particular, result. In the process, the overmolding material can be provided, e.g., by fluidizing a granule.

The overmolding preferably takes place by means of an injection molding method—in particular, by a so-called "hotmelt molding" or "macromelt molding" or by low-pressure molding technology. In the process, the term "hotmelt" refers in general to the use of hotmelt adhesives and also comprises such hotmelt adhesives that are also known as so-called "macromelts."

The overmolding preferably takes place by a technology which is between conventional injection molding and two-component molding and differs from these methods in terms of the applied pressures and cycle times. The pressure is preferably lower than in the case of classical injection molding, and the cycle time is preferably less than in the case of two-component molding. In the case of so-called "macromelt molding," a thermoplastic hotmelt adhesive can be used which consists preferably of renewable raw materials. The application can take place via a purely thermal fusion method without chemical reactions, and without having to release pollutants.

In the case of overmolding, an injection temperature is preferably selected such that a surface (outer lateral surface) of the wall is at least partially fused. As a result, the overmolding can be connected to the wall effectively—in particular, by mechanical adhesion. Optionally, in the process, a chemical bond can be established between the components, if desired.

According to one embodiment, the overmolding is carried out in two stages, by means of, in a first step (in particular, in a pre-molding step), overmolding at least the sensor device—in particular, such that the sensor device is provided in a functional arrangement—and then, in a second step (in particular, in a main molding step), overmolding at least the lead also, wherein the overmolding is preferably brought into a final form. As a result, first, a functional overmolding can take place such that the sensor device is functional, and then, the overmolding can be fully formed—in particular, in order to form an integral housing and/or to position all components securely relative to one another and/or to introduce a large quantity of overmolding material at high speed. By means of the two-stage method, shrink marks can be prevented, which provides advantages, in particular, with regard to a large quantity of overmolding material. Also, the first overmolding can take place at a lower speed and with greater precision and metering, as a result of which, for example, a more precise positioning can take place, or as a result of which it is possible to impart specified material characteristics to the overmolding in a controlled manner.

According to one embodiment, prior to the overmolding, a mandrel is inserted into the lead. As a result, a stabilization of the lead, in particular, can be ensured. The overmolding can be provided on the lead in a state of the lead that corresponds to the operating state of the lead, even if the lead is exposed to an increased pressure and/or an increased temperature during the overmoiding. The mandrel can ensure a counter-pressure and stabilize the wall from the inside. Also, the wall can be aligned by means of the mandrel and/or be placed in a predetermined geometry, e.g., with a slight curvature as well. It turns out that the connection between the outer lateral surface of the wall and the overmolding material can be influenced by the diameter of the mandrel. It turns out that a comparatively large mandrel diameter leads to an especially good adhesion.

It is also possible to set the force exerted on the wall during overmolding by means of the mandrel diameter. It is also possible to set the extent to which the wall should yield to an increased pressure from the outside on the outer lateral surface of the wall. In particular, the lead/hose geometry can be "frozen," even if overmoiding is performed at comparatively high pressures in the range of 20 bar (2 MPa) and/or high temperatures in the range of 180°-200°. Preferably, the mandrel diameter is dimensioned both with regard to a clamping force of the overmoiding tool, as well as with regard to an inside diameter of the wall. In other words, the diameter of the mandrel is preferably selected such that an optimal clamping pressure is achieved, so that the adhesion of the overmoiding material on the outer lateral surface of the wall is at the maximum. Preferably, the mandrel diameter is somewhat smaller than the inside diameter of the wall.

Preferably, the overmolding tool has two jaws or molded parts, which each provide a part of a negative mold and which can be mounted on one another. Preferably, the overmolding tool has protruding sections to form recesses in the overmolding, wherein the protruding sections preferably have a concave surface, each being designed to geometrically correspond to the outer lateral surface of the wall.

According to one embodiment, prior to the overmolding, a radial cavity for receiving a sensor of the sensor device is placed in the wall, and the sensor is arranged in the radial cavity, wherein the sensor device is preferably fixed—in particular, firmly bonded—outside on the wall. As a result, a measuring system with advantageous measuring characteristics can be provided, and the positioning and the overmolding of the sensor device in the desired (predefined) position relative to the lead can be simplified, especially since the sensor device does not necessarily have to be held in a specific position within a tool. According to one variant, the radial cavity is sealed fluid-tight by means of the sensor device prior to overmolding—in particular, by means of an interference fit.

According to one embodiment, the overmolding is applied on an outer lateral surface of the wall such that the overmolding adheres to the outer lateral surface of the wall—in particular, by mechanical adhesion—wherein, during overmolding, a temperature preferably in the range of 150° to 220° and/or a pressure in the range of 5 bar (0.5 MPa) to 25 bar (2.5 MPa) is set. As a result, the overmolding can be connected to the wall in one unit, and the relative position of the overmolding relative to the lead, and also, as a result, the relative position of further components of the measuring system to one another, can be clearly defined. It turns out, that an adhesion, in the process, can be ensured to be essentially separate from any specified surface condition of the wall (structure, roughness).

According to one embodiment, during overmolding, a temperature in the range of 150° to 220° and/or a pressure in the range of 5 bar (0.5 MPa) to 25 bar (2.5 MPa) is set. As a result, for one thing, a large quantity of overmolding material can be placed, and, for another thing, the overmolding can take place such that the wall connects to the overmolding material—in particular, by physical binding or mechanical adhesion. In the process, the overmold method can be defined by further parameters such as a specified dwell time, a specified cooling time, a specified injection speed, and/or a specified tool temperature.

According to one embodiment, during overmolding, the following process parameters are set, wherein reference is made to a two-stage overmold method comprising a pre-molding step and a main molding step:

Tank Temperature:
180° to 200° Celsius (both during pre-molding, as well as during main molding); Pre-melt zone: 180° to 200° Celsius (pre-molding and main molding);
Lead temperature: 180° to 200° Celsius (pre-molding and main molding);
Head temperature: 180° to 200° Celsius (pre-molding and main molding);
Injection Pressure:
20 bar (2 MPa) to 30 bar (3 MPa)—in particular, 25 bar (2.5 MPa) (pre-molding and main molding);
Dwell Time:
5 sec to 15 sec (both during pre-molding, as well as during main molding);
Cooling Time:
50 sec to 70 sec during pre-molding, 15 sec to 30 sec during main molding;
Melt pressure: 15 to 20 bar (1.5 to 2 MPa) during pre-molding, 20 to 30 bar (2 to 3 MPa) during main molding;
Tool temperature: 45° to 55° Celsius (pre-molding and main molding);

The mentioned cooling times can ensure a good cohesion within the overmolding, even in the case of a comparatively large quantity of overmolding material. The good cohesion can also ensure a good deformation resistance of the overmolding.

According to one embodiment, during arrangement in the (overmolding) tool, a relative positioning of the sensor device relative to the (overmolding) tool takes place, especially in relation to a negative mold for the formation of an opening in the overmolding, e.g., in relation to a pin extending in radial direction at least approximately vertically/orthogonally to the central longitudinal axis of the lead. As a result, in the case of a sensor device embedded in the overmolding, a communications path between the sensor and the surrounds can be easily ensured. The position of the sensor device within the overmolding can, in the process, to a large extent be randomly selected.

In accordance with one method variant, a tank receiving the overmolding material is tempered to approximately 170-180° C. (in particular, permanently). The lead is heated up to approximately 190°-210°—in particular, to 200° C. (in particular, temporarily). A nozzle of the overmolding tool is, for example, heated up to 200° to 220°—in particular, to 210° C. (temporarily). The pressure set in the overmolding tool, or the applied pressure, is, for example, between 5 bar (0.5 MPa) and 20 bar (2 MPa). The tool itself can likewise be tempered, e.g., to approximately 25° to 35°—in particular, to 30° C.

According to one embodiment, while being arranged in the tool, the lead is fastened on at least one holding fixture of the (overmolding) tool—in particular, a retaining bracket or a retaining clip of a negative mold of the (overmolding) tool. As a result, the lead can be arranged in a predefined TARGET geometry or alignment relative to the tool and relative to the overmolding. Preferably, the tool is formed in two parts of an upper part and a lower part.

In the following figures, the invention will be explained in greater detail with the help of exemplary embodiments. In connection with the description, in the case of the individual reference numbers, where not explicitly explained, reference is made to the exemplary embodiment of FIG. 1 or to the additional figures. These show:

BRIEF DESCRIPTION OF THE FIGURES

FIGS. 3A, 3B, 3C each shows, in a perspectival view, a receptacle for connecting a sensor device of the measuring system shown in FIG. 1 to an energy source and/or to communications means, e.g., via a cable or a wireless connection;

FIGS. 4A and 4B show, in a perspectival view and in a perspectival cutaway view, individual components of the measuring system shown in FIG. 1;

DETAILED DESCRIPTION OF THE DRAWINGS

Figure 1:
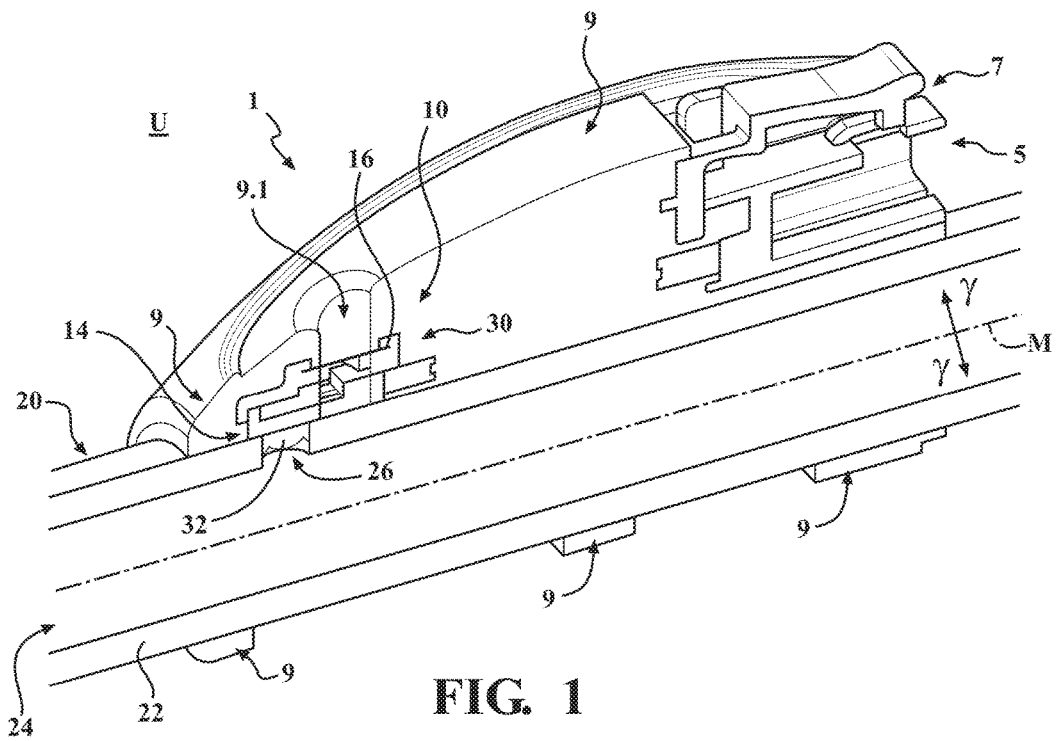
FIG. 1 shows, in schematic representation in perspectival cutaway view, a measuring system according to one exemplary embodiment of the invention.

FIG. 1 shows a medical technology measuring system 1 comprising a lead 20 extending in longitudinal direction along a central longitudinal axis M and a measuring device 10 with a sensor device 30. The lead 20 is explained in FIG. 1 using the example of a hose lead. The sensor device 30 has a sensor 32 which is arranged in a radial cavity 26 within a wall 22 of the lead 20. The radial cavity 26 extends in radial direction r and is designed in the shape of an opening, a hole, or a borehole in the wall 22. The sensor 32 is configured to measure a characteristic—in particular, a pressure of a fluid guided in a longitudinal cavity 24 within the lead 20. The measuring system 1 further comprises a receptacle 5 and a button 7.

The measuring system 1 has an overmolding 9, which surrounds the sensor device 30 and, at least partially, also the receptacle 5 and the button 7. The overmolding 9 is in contact with the wall 22, at least in sections. The overmolding 9 surrounds the wall 22, at least in sections—in particular, at three different points, viz., right at the front, approximately in the middle, and at the rear of the arrangement depicted. The overmolding 9 has an aperture 9.1 or an opening, through which the sensor 32 is in communication with the surroundings U. The aperture 9.1 is arranged in the region of a cover/protective cap 14—in particular, in the region of a membrane 16 of the sensor device 30—and extends essentially in a radial direction.

Figure 2A:
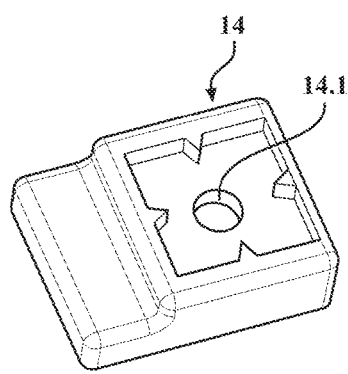
FIGS. 2A, 2B, 2C each shows, in a perspectival view, a protective cap for covering a sensor device of the measuring system shown in FIG. 1, or a membrane for the protective cap.
Figure 2B:
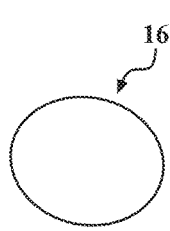
Figure 2C:
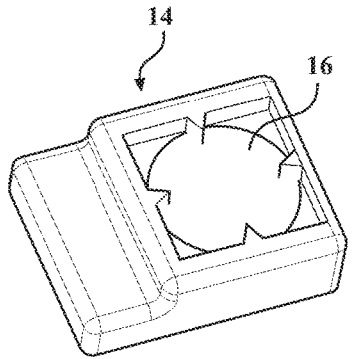

In FIGS. 2A, 2B, and 2C, the components protective cap 14 and membrane 16 are shown in detail. The protective cap 14 has an opening 14.1—in particular, in the shape of a vent bore. The preferably gas-permeable, fluid-tight membrane 16 is arranged above the opening 14.1 and covers it completely. The membrane 16 can in the process be fastened at several points on an outer edge—in particular, on lugs or hooks protruding inward in a radial direction.

In FIGS. 3A, 3B, and 3C, the components receptacle 5 and button 7 are shown in detail. The button 7 can be arranged on the receptacle 5. An underside of the button 7 is designed to geometrically correspond to an upper side of the receptacle 5.

Figure 4B:
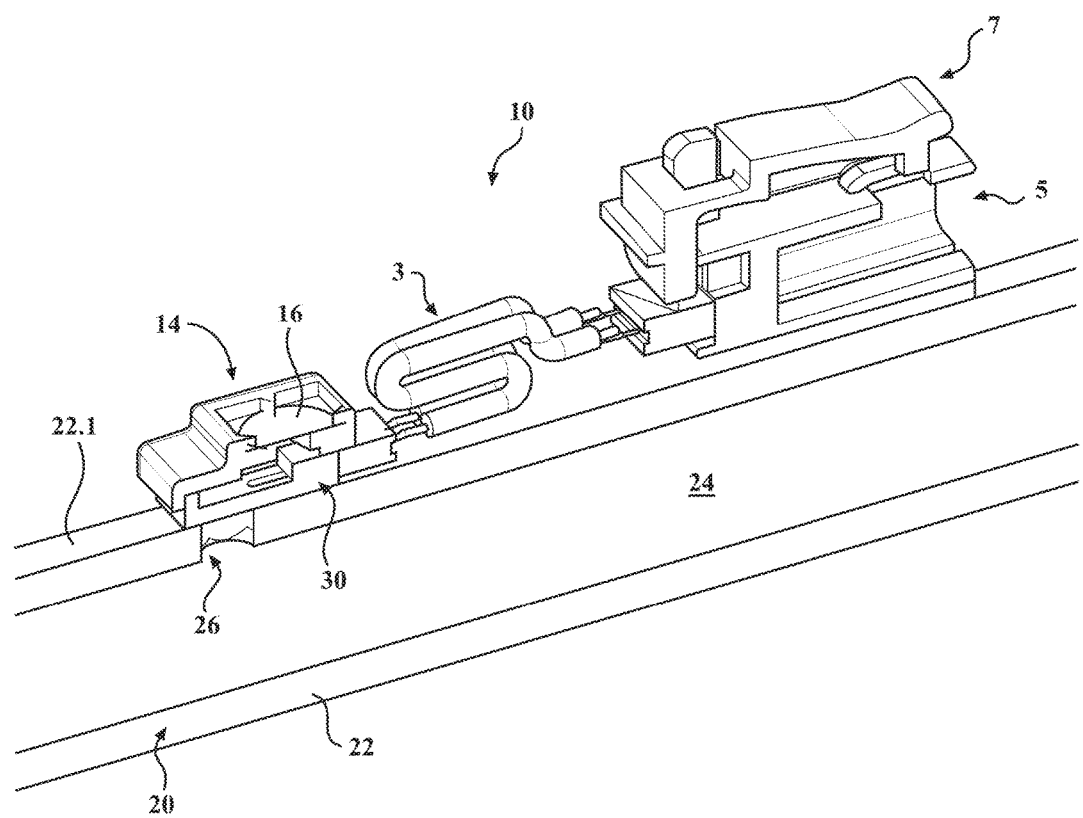

In FIGS. 4A and 4B, yet another component of the measuring device 10 is shown. The measuring device 10 also comprises an adapter cable 3, which is arranged between the receptacle 5 and the sensor device 30 and which connects the sensor device 30 electrically to a power supply and/or communications interface (not shown). The adapter cable 3 is arranged in loops or windings or in a serpentine manner, with excess length between the receptacle 5 and the sensor device 30, as a result of which relative movements, due, for example, to a bend of the lead 20, can be compensated for.

Figure 5:
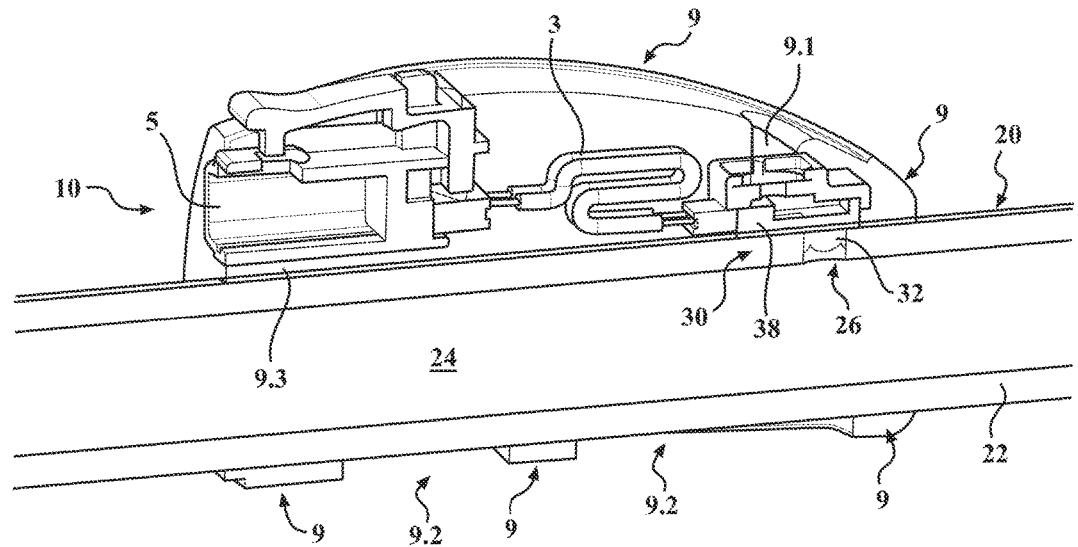
FIG. 5 shows, in schematic representation in perspectival cutaway view, a measuring system according to one exemplary embodiment of the invention, wherein an overmolding is illustrated.

FIG. 4B shows in detail that the sensor device 30 is in contact with an outer lateral surface 22.1 of the lead 20, whereas the adapter cable 3 and the receptacle 5 are embedded in the overmolding, as shown in FIG. 5.

FIG. 5 shows the overmolding 9 in cross-section. The adapter cable 3 and the receptacle 5 are embedded in the overmolding 9 and do not touch the lead 20. As a result, friction from these components on the wall 22 can be prevented. Between the receptacle 5 and the wall 22, an intermediate section 9.3 is designed, which positions the receptacle 5 relative to the wall 22. In contrast to this, the sensor device 30 has a contact section 38 which is arranged outside on the wall 22 and is preferably firmly bonded to the wall 22. In this way, the radial position of the sensor 32 within the radial cavity 26 can bedefined in an exact manner, and a relative movement between the wall 22 and the sensor device 30 can be avoided. This can ensure a good fluid-tightness and a clear position of the sensor 32, and thus an exact measurement. Simultaneously, the overmolding 9 can ensure that no radial or axial forces are exerted externally on the sensor device 30. The overmolding 9 can protect the sensor device 30 from external influences and ensure the predefined position of the sensor device 30 relative to the wall 22 by preventing relative movements between the sensor device 30 and the wall 22.

On an underside of the wall 22, the overmolding has 9 two recesses 9.2. These recesses 9.2 can, on the one hand, minimize material consumption; on the other hand, a flexibility of the lead 20 can be maintained, or tension due to deformations in the overmolding can be minimized.

Figure 6A:
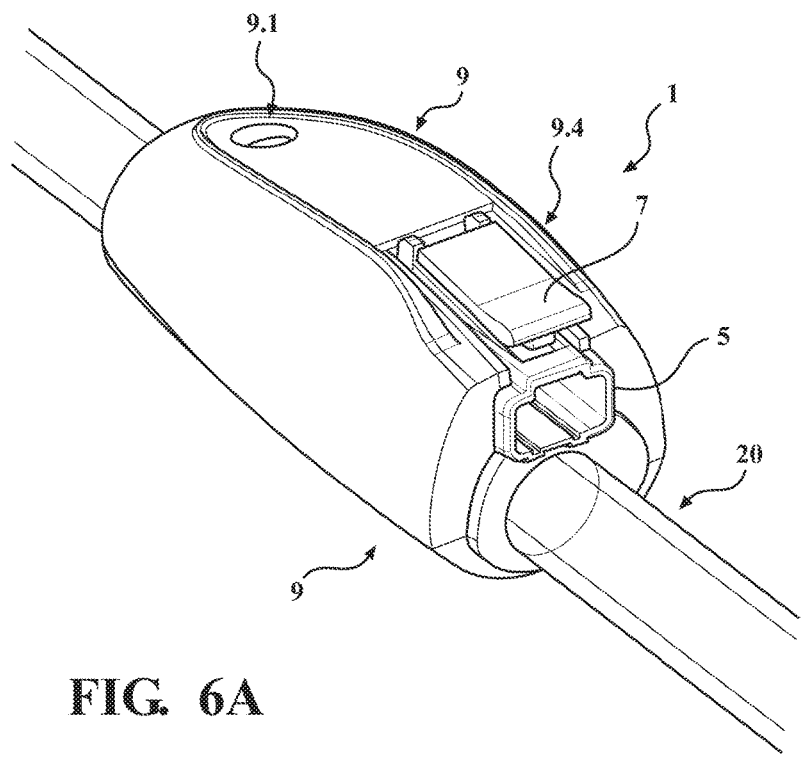
FIGS. 6A and 6B each shows, in a perspectival view, a measuring system according to one exemplary embodiment of the invention.
Figure 6B:
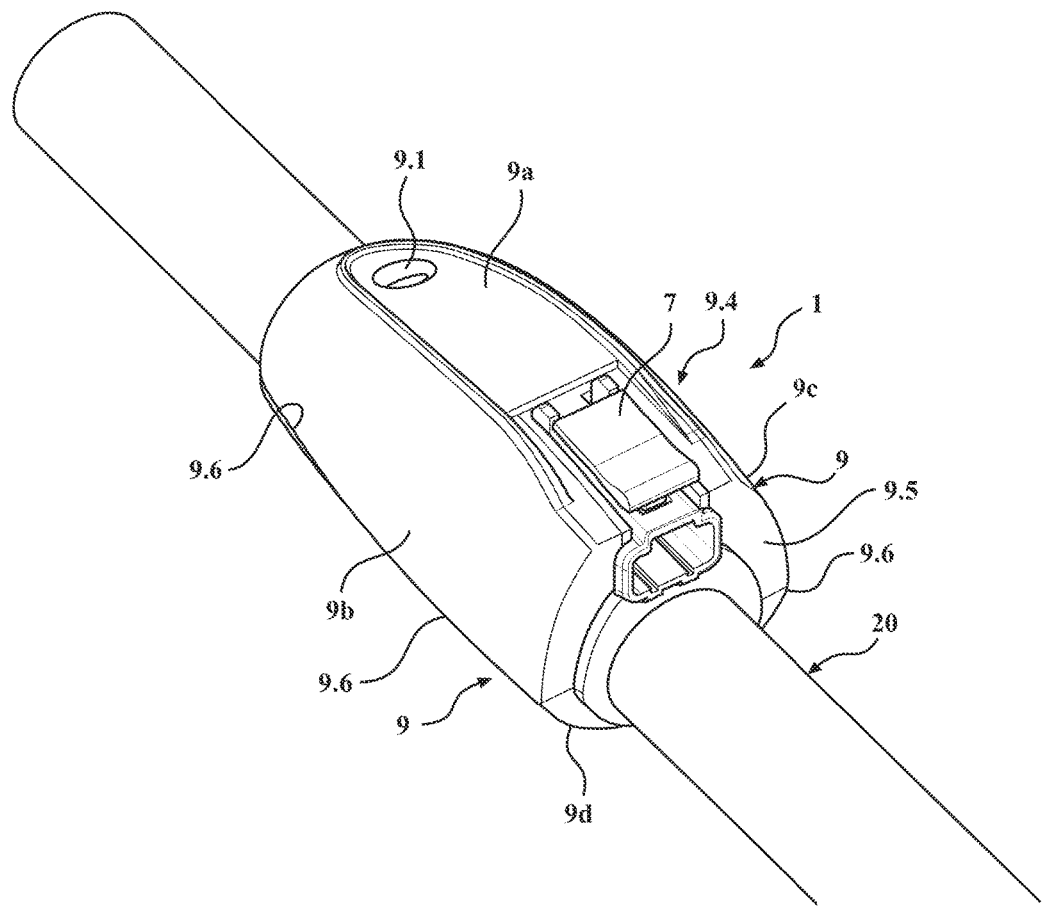

In FIGS. 6A and 6B, the overmolding 9 is shown from a view of a rear, proximal side, at which the receptacle 5 can be connected to a cable or a (communications) stick. The receptacle 5 shown in the figures is configured to receive either a connector together with an (external) cable, or a type of "stick" or module. The stick can ensure a wireless communication, e.g., via WLAN, radio, or Bluetooth. The stick can also have a power supply, e.g., a battery. The receptacle 5 can, in the process, have the same shape for both variants, so that a user can decide whether a wired power supply and communication is desired, or whether the communication should take place wirelessly and the power supply should take place via the stick, e.g., by means of batteries integrated the stick. Both the cable and the stick can, in the process, be used multiple times. In other words, the medical technology measuring system 1 or the medical technology measuring device 10 can be provided for a single ("disposable") use, and, prior to disposal, the cable or the stick can then be decoupled from the receptacle.

The overmolding 9 surrounds the lead 20 completely. At an upper side, the overmolding 9 has a notch or a recess 9.4 for receiving the button 7. A proximal front end section 9.5 of the overmolding 9 is arranged on the same radial plane as a proximal end of the receptacle 5. The overmolding 9 and the receptacle 5 are arranged flush, on the same plane. This can ensure a compact arrangement, and edges or protrusions can be integrated in the overmolding 9, so that a user does not come into contact with the edges.

The overmolding 9 has several surface sections—in particular, four different surface sections. A surface section 9a on the upper side provides coverage and the aperture 9.1. Lateral surface sections 9b, 9c provide flanks or holding surfaces, at which the overmolding 9 can be grasped and held in an ergonomic manner. A surface section 9d on the lower side provides a roundness and an underside, upon which the overmolding 9 can be placed, e.g., in the case of connecting the receptacle 5 to a cable. The respective lateral surface section 9b, 9c adjoins on an edge 9.6 the lower surface section 9d. The edge 9.6 extends in a longitudinal direction along the entire overmolding 9 and can provide an ergonomic negative mold for the inner surface of a human hand. In cross-section, the overmolding 9 is designed in the shape of a rhombus with convex, round surface sections.

Figure 7A:
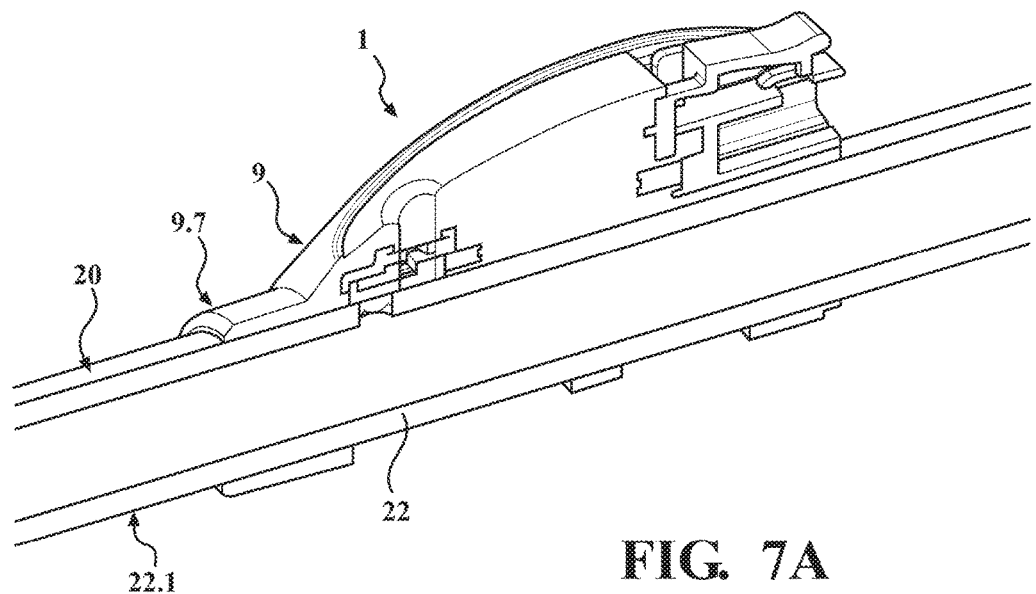
FIGS. 7A and 7B each shows, in a perspectival view, a measuring system according to a further exemplary embodiment of the invention.
Figure 7B:
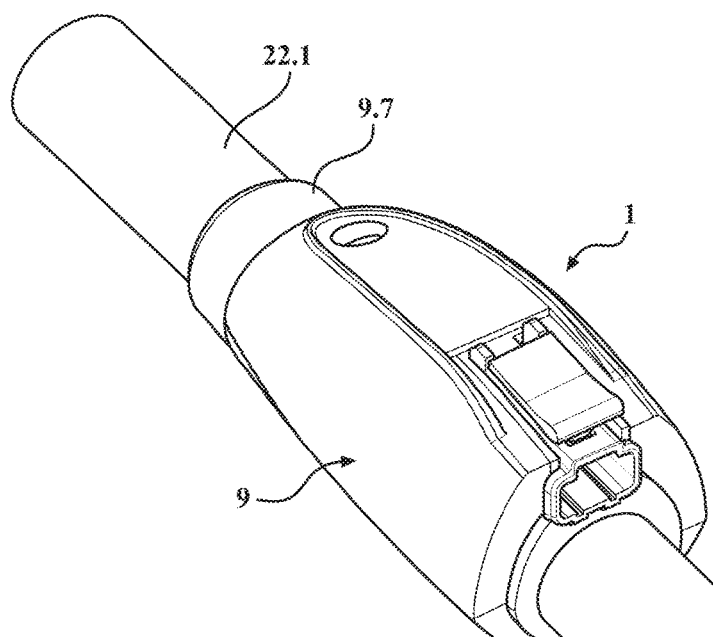

FIGS. 7A and 7B show an exemplary embodiment in which the overmolding 9 has an extension 9.7. The extension 9.7 is provided on a distal end of the overmolding and comes into contact with an/the outer lateral surface 22.1 of the wall 22. Optionally—and also, in addition—the extension can also be provided on a proximal end of the overmolding.

Figure 9:
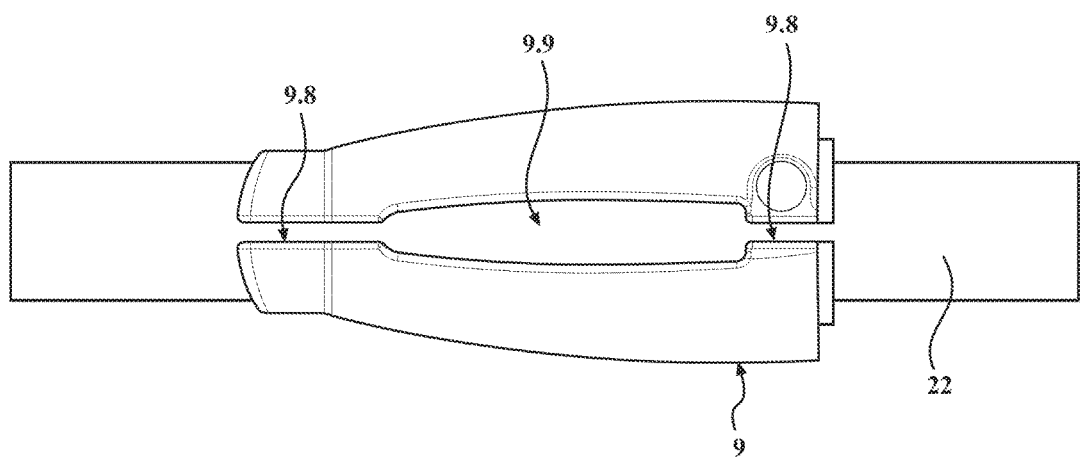
FIG. 9 shows, in schematic representation, in view of the underside, a measuring system according to one exemplary embodiment of the invention, wherein an overmolding is illustrated.

FIG. 9 shows an exemplary embodiment in which the overmolding 9 has a continuous slot 9.8 on an underside of the wall 22 running parallel to the longitudinal extension of the wall 22. This slot 9.8 is broadened to a window 9.9 in a central region, as a result of which, in this region, the wall 22 is continuously visible. If the wall 22 is made of a transparent material, then a constant view of the sensor 32 is possible in the radial cavity 26 of a fluid guided in the lead 20. Further, the slot 9.8 can also act as an expansion joint in a longitudinal direction, which rules out the danger of a movement related crack formation.

Figure 8:
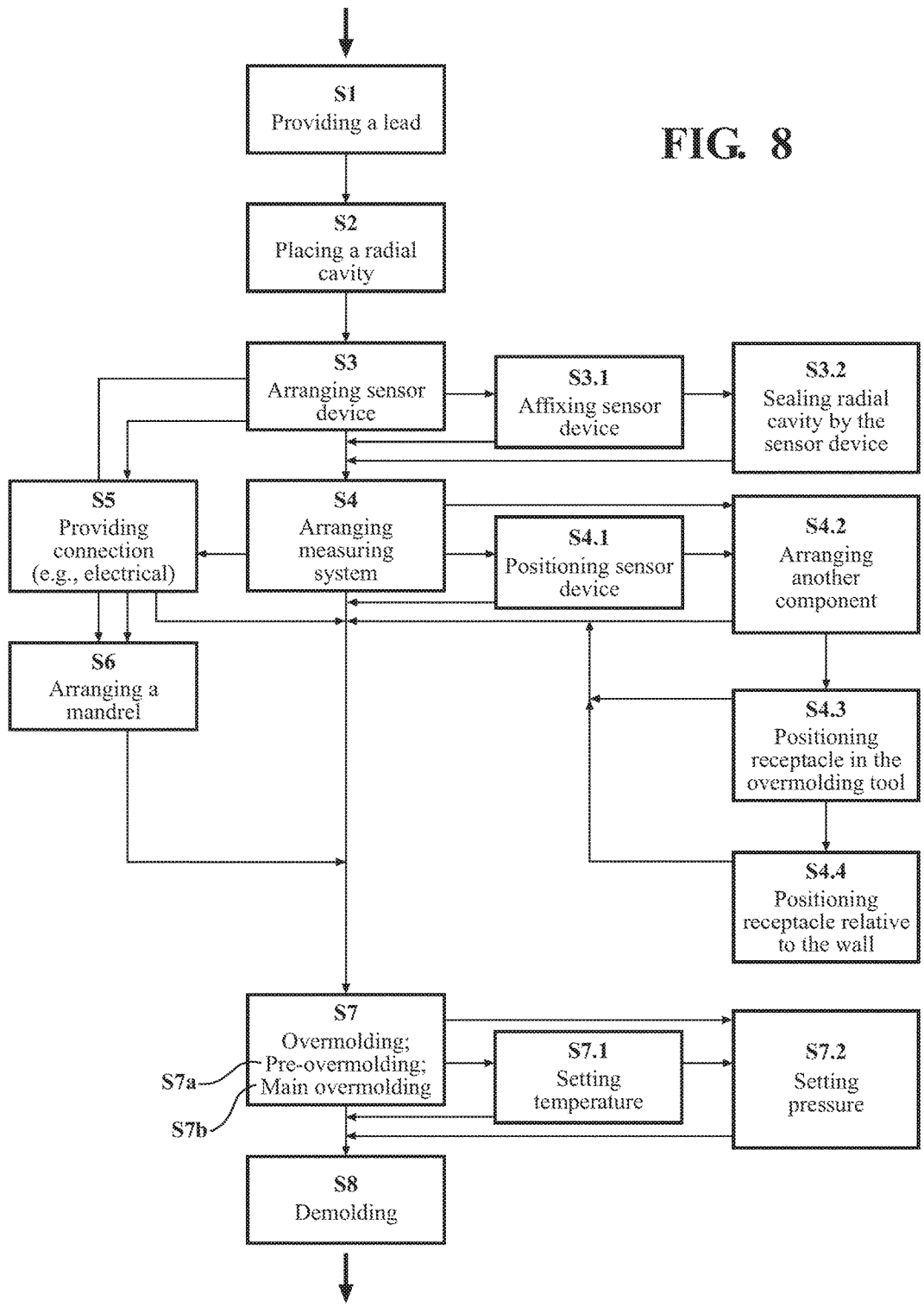
FIG. 8 shows, in schematic representation, a method diagram for steps of a method according to exemplary embodiments of the invention.

FIG. 8 shows steps of a method for producing a medical technology measuring system. The method comprises one or more of the steps described in the following.

In a step S1, provision is made for a lead that is equipped to guide a fluid in particular, blood. In a step S2, placement of a radial cavity in a wall of the lead occurs, e.g., by boring. In a step S3, an arrangement of a sensor device and, optionally, further components of the measuring system on the lead occurs—in particular, on an outer lateral surface of the wall. In the process, the measuring device can be fixed on the wall in a step S3.1—in particular, in a firmly bonded manner by means of an adhesive agent. Further, the radial cavity can be sealed in a step S3.2 in particular, by means of a radial section of the sensor device forming an interference fit with the radial cavity. In the process, an adhesive agent is preferably not provided. Steps S3.1 and S3.2 can be carried out independently of one another or in combination with one another. In a subsequent Step S4, an overmolding tool can be provided and the measuring system can be arranged together with the lead in the overmolding tool. In the process, in a step S4.1, a negative mold and a holding fixture of the tool may be provided A retaining bracket or retaining clip may also be provided at this step. A relative positioning of the sensor device in the overmolding tool can take place in particular, in relation to a protruding (in particular, radially aligned) pin or in conjunction with an arrangement of the pin for the formation of an opening in the overmolding. In addition, in a step S4.2, at least one further component of the measuring system in particular, a receptacle and/or an adapter cable-can also be arranged in the overmolding tool, and, in a step S4.3, positioned relative to the overmolding tool, and/or, in a step S4.4, the receptacle can be positioned relative to the outer lateral surface of the wall.

The receptacle of the measuring system can be positioned relative to the lead in the case of arrangement on the lead, and, optionally, in conjunction with a button and/or an adapter cable. The receptacle can, in the process, be positioned spaced at a radial distance to an outer lateral surface of the wall. Preferably, the radial distance is at least 1.0 mm. It turns out that this distance is sufficiently large that the overmolding material can be placed in the intermediate space between the wall and the receptacle.

In a step S5, the individual components can be connected to one another. In particular, the sensor device can be connected to an adapter cable, and the adapter cable can be connected to the receptacle. The step S5 can, in the process, also be carried out before the step S4.

After the arrangement of the measuring system in the tool has taken place, and the tool has been closed, in a step S7, an overmolding can occur. The step S7 can, in the process, be characterized by the following steps: Step S7a, corresponding to a procedural step of a pre-overmolding (first overmolding step), Step S7b, corresponding to a procedural step of a main overmolding (second overmolding step), Step S7.1, corresponding to a procedural step of setting a specific temperature in the case of overmolding, Step S7.2, corresponding to a procedural step of setting a specific pressure in the case of overmolding. Optionally, prior to overmolding—in particular, also prior to Step S4 in a step S6, a mandrel can be provided and an arrangement of the mandrel in a longitudinal cavity of the lead can take place. The overmolding can, in the process, be controlled by setting a specific temperature (Step 7.1) and/or by setting a specific pressure (Step 7.2). Finally, in a step S8, a demolding can take place—in particular, after a predetermined cooling time.

LIST OF REFERENCE SYMBOLS

1 Medical technology measuring system
3 Adapter cable
5 Receptacle
7 Button
9 Overmolding
9a Surface section on the upper side
9b, 9c Lateral surface section
9d Surface section on the lower side
9.1 Opening or aperture in overmolding
9.2 Recess on underside
9.3 Intermediate section
9.4 Recess or notch on upper side
9.5 Proximal front end or front end section
9.6 Edge
9.7 Extension or edge
9.8 Slot
9.9 Window on underside
10 Medical technology measuring device
14 Cover—in particular, protective cap
14.1 Opening—in particular, vent bore
16 Gas-permeable, fluid-tight membrane
20 Lead—in particular, a hose lead
22 Wall
22.1 Outer lateral surface of the wall
24 Longitudinal cavity along the central longitudinal axis for guiding the flid
26 Radial cavity—in particular, opening or recess
30 Sensor device
32 Sensor
38 Contact section
M Central longitudinal axis
r radial direction
S1 Procedural step of providing a lead
S2 Procedural step of placing a radial cavity
S3 Procedural step of arranging a sensor device on the lead
S3.1 Procedural step of affixing the sensor device on the lead
S3.2 Procedural step of sealing the radial cavity by means of the sensor device
S4 Procedural step of arranging the measuring system with the lead in an overmolding tool
S4.1 Procedural step of relative positioning of the sensor device in the overmolding tool
S4.2 Procedural step of arranging at least one further component of the measuring system in the overmolding tool
S4.3 Procedural step of relative positioning of the receptacle in the overmolding tool
S4.4 Procedural step of relative positioning of the receptacle relative to the outer lateral surface of the wall
S5 Procedural step of connection—in particular, electrical connection—of individual components of the measuring system to one another
S6 Procedural step of arranging a mandrel in the longitudinal cavity of the lead
S7 Procedural step of overmolding
S7a Procedural step of a pre-overmolding (first overmolding step)
S7b Procedural step of a main overmolding (second overmolding step)
S7.1 Procedural step of setting a specific temperature in the case of overmolding
S7.2 Procedural step of setting a specific pressure in the case of overmolding
S8 Procedural step of demolding
U Surroundings

The invention claimed is:

1. A medical technology measuring system, comprising:
   a measuring device for measuring a characteristic of a fluid, wherein the measuring device comprises:
   a lead, which extends along a central longitudinal axis and is configured to guide a fluid within a longitudinal cavity bounded by a wall, and
   a sensor device with a sensor, which is equipped to measure a characteristic of the fluid guided in the longitudinal cavity; and
   an overmolding at least partially surrounding the measuring device,
      wherein the lead has a radial cavity incorporated in the wall in a radial direction, and at least the sensor of the sensor device is arranged and is integrated in the wall such that the sensor is in communication with the fluid guided in the longitudinal cavity.

2. The measuring system according to claim 1, wherein the overmolding surrounds both at least the sensor device and a section of the lead.

3. The measuring system according to claim 1, wherein the overmolding is provided on the lead such that the overmolding surrounds at least the sensor device of the measuring device, wherein at least the sensor device is positioned and embedded in a predefined position relative to the lead in the overmolding.

4. The measuring system according to clam 1, wherein the overmolding is made of a hotmelt adhesive.

5. The measuring system according to claim 4, wherein the overmolding is made of a mixture of polyester and hydrocarbon resin, with a greater part polyester than hydrocarbon resin.

6. The measuring system according to claim 1, wherein the overmolding is configured to adhere to an outer lateral surface of the wall by mechanical adhesion.

7. The measuring system according to claim 1, wherein the overmolding completely surrounds at least the lead on at least two sections of the overmolding spaced apart from one another.

8. The measuring system according to claim 1, wherein the overmolding completely surrounds at least the lead on two free ends of the overmolding arranged at a maximum distance from one another.

9. The measuring system according to claim 1, wherein the overmolding has an extension or edge on a proximal and/or distal end or section of the overmolding, which comes into contact on an outer lateral surface of the wall.

10. The measuring system according to claim 1, wherein the overmolding has an opening extending in a radial direction, at least approximately vertically to the central longitudinal axis, wherein the opening provides a connection between the sensor and the surroundings.

11. The measuring system according to 10, wherein the measuring system has an adapter cable connected to the sensor device, the adapter cable being embedded in the overmolding, and the adapter cable being arranged with an excess length in a serpentine line in the overmolding.

12. The measuring system according to claim 1, wherein the measuring system has a receptacle, and wherein the overmolding at least partially surrounds the receptacle and is also disposed between the lead and the receptacle.

13. The measuring system according to claim 1, wherein the measuring device is a disposable device provided for single use, wherein the sensor device has a coupling point for communication and/or a power supply for a wired transmission via a cable or for a wireless transmission.

14. The measuring system according to claim 1, wherein the fluid is blood.

15. The measuring system according to claim 1, wherein the characteristics of the fluid is pressure.

16. A method for producing a measuring system according to claim 1, comprising the steps of:
   providing a lead equipped to guide a fluid;
   arranging a sensor device of the measuring system on an outer lateral surface of a wall of the lead;
   arranging the measuring system with the lead in a tool;
   overmolding at least the sensor device and the lead, at least in sections, with a material based upon polyester and hydrocarbon resin.

17. The method according to claim 16, wherein the step of overmolding comprises two steps:
   overmolding at least the sensor device such that the sensor device is provided in a functional arrangement, and
   overmolding at least the lead, wherein the overmolding is brought into a final form, and wherein, prior to overmolding, a mandrel is inserted into the lead.

18. The method according to claim 17, wherein the lead is fastened on a retaining bracket or a retaining clip of the negative mold of the tool.

19. The method according to claim 16, wherein the step of arrangement in the tool further comprises:
   a relative positioning of the sensor device relative to the tool in relation to a negative mold for the formation of an opening in the overmolding, wherein the lead is fastened on at least one holding fixture of the tool.

20. A medical technology measuring system, comprising:
   a measuring device for measuring a characteristic of a fluid, wherein the measuring device comprises:
   a lead, which extends along a central longitudinal axis and is configured to guide a fluid within a longitudinal cavity bounded by a wall, and
   a sensor device with a sensor, which is equipped to measure a characteristic of the fluid guided in the longitudinal cavity; and
   an overmolding at least partially surrounding the measuring device,
      wherein the overmolding has an opening extending in a radial direction, at least approximately vertically to the central longitudinal axis, the opening providing a connection between the sensor and the surroundings, the measuring system has an adapter cable connected to the sensor device, the adapter cable being embedded in the overmolding, and the adapter cable being arranged with an excess length in a serpentine line in the overmolding.

21. A medical technology measuring system, comprising:
   a measuring device for measuring a characteristic of a fluid, wherein the measuring device comprises:
   a lead, which extends along a central longitudinal axis and is configured to guide a fluid within a longitudinal cavity bounded by a wall, and
   a sensor device with a sensor, which is equipped to measure a characteristic of the fluid guided in the longitudinal cavity, and
   an overmolding at least partially surrounding the measuring device,
      wherein the measuring device is a disposable device provided for single use, and the sensor device has a coupling point for communication and/or a power supply for a wired transmission via a cable or for a wireless transmission.

22. A medical technology measuring system, comprising:
   a measuring device for measuring a characteristic of a fluid, wherein the measuring device comprises:
   a lead, which extends along a central longitudinal axis and is configured to guide a fluid within a longitudinal cavity bounded by a wall, and
   a sensor device with a sensor, which is equipped to measure a characteristic of the fluid guided in the longitudinal cavity; and
   an overmolding at least partially surrounding the measuring device,
      wherein the measuring system has a receptacle, and wherein the overmolding at least partially surrounds the receptacle and is also disposed between the lead and the receptacle.

* * * * *